United States Patent [19]

Pigneul

[11] Patent Number: 4,496,359
[45] Date of Patent: Jan. 29, 1985

[54] SANITARY ARTICLES TO ABSORB BODY LIQUIDS

[75] Inventor: Raymond Pigneul, Durrenentzen, France

[73] Assignee: Beghin-Say S.A., Thumeries, France

[21] Appl. No.: 445,374

[22] PCT Filed: Mar. 19, 1982

[86] PCT No.: PCT/FR82/00055
§ 371 Date: Nov. 18, 1982
§ 102(e) Date: Nov. 18, 1982

[87] PCT Pub. No.: WO82/03170
PCT Pub. Date: Sep. 30, 1982

[30] Foreign Application Priority Data

Mar. 19, 1981 [FR] France ............................... 81 05477

[51] Int. Cl.³ .............................................. A61F 13/16
[52] U.S. Cl. .................................................. 604/387
[58] Field of Search .............. 604/386, 387, 389, 390, 604/385, 378

[56] References Cited

U.S. PATENT DOCUMENTS

| 3,814,100 | 6/1974 | Nystrand et al. | 604/385 |
| 4,246,900 | 1/1981 | Schroder | 604/389 |
| 4,285,343 | 8/1981 | McNair | 604/387 |

FOREIGN PATENT DOCUMENTS

| 2134748 | 12/1972 | France . |
| 2374890 | 7/1978 | France . |
| 2388515 | 11/1978 | France . |

*Primary Examiner*—John D. Yasko
*Attorney, Agent, or Firm*—A. W. Breiner

[57] ABSTRACT

Sanitary articles to absorb body liquids.

They comprise an external liquid-impermeable sheet (2) enveloping the absorbing pad (1) not only across all of its surface (1b) opposite the human body and over all its thickness, but also it is applied as a pleat on the longitudinal edges of the pad side (1a) facing the human body.

Menstrual napkins, pilches.

7 Claims, 5 Drawing Figures

SANITARY ARTICLES TO ABSORB BODY LIQUIDS

The present invention relates to sanitary articles to absorb body liquids. Quite particularly it is suited to the manufacture of single-use articles such as menstrual napkins and disposable pilches.

Such articles evince a stratified structure consisting of a pad absorbing and retaining liquids (cellulose fiber mattress) located between a liquid-permeable sheet in contact with the human body and an external liquid-impermeable sheet. Means assuring that the article will be well kept in place on the body are added to this structure.

For instance, in the case of a menstrual napkin, provision is made for one or more continuous or interrupted lines of adhesive to fasten the napkin to some piece of underwear. The lines of adhesive most of the time are arranged in the median part, that is closer to the longitudinal axis of the napkin than to its edges.

Considering the anatomical differences between users, it is impossible to avoid substantial deformations in the napkin's absorbing mass. These large deformations degrade the absorption of the body liquids and cause leaks, soiling the underwear.

The leaks also are enhanced because there is no efficacious barrier in the lateral zones of the absorbing mass.

To remedy these drawbacks, the present invention recommends a novel structure for an absorbing article whereby the external liquid-impermeable sheet encloses the absorbing-mass pad across its entire thickness and also is applied against the longitudinal edges of the pad side facing the human body (i.e., the pad inside).

The absorbing-mass pad accordingly is completely inserted, exception made of the absorption surface facing the human body, in an impermeable "pocket" which at the same time also is the article's outer wrap. Such an arrangement reinforces the "pocket" effect across the entire thickness of the absorbing mass.

In the preferred embodiment of the invention, the external impermeable sheet comprises sideways extensions obtained by folding its lateral parts above the longitudinal edges of the pad side facing the body, said sideways extensions constituting, on either side and beyond the surface bounded by the absorbing pad, supports for the lines of adhesive, whether continuous or interrupted, which serve to fasten the napkin to the underwear.

Such an arrangement of the lines of adhesive outside the surface bounded by the absorbing-mass pad makes it possible to keep the largest surface possible of the absorbing pad in contact with the body (the napkin is stressed laterally).

Preferably, the lines of adhesive are arrayed at particular distances from the pad's edges substantially equal to the pad thickness in the compressed state. Such an arrangement offers the advantage of applying the napkin's longitudinal edges under pressure against the user's body and consequently to reinforce both the reliability (fewer chances of lateral leaks) and the absorption (good contact between the absorbing mass and the user's body). Moreover, the menstrual napkin, being kept in place by two external lines of adhesive on the surface of the pad, tends to curve toward the user's body, further reinforcing the absorption effect.

The invention also applies to disposable pilches in that it permits eliminating more effectively the lateral leaks, in that it enhances the absorption and the retention by the "pocket" effect of the new structure.

In same manner as applies to a menstrual napkin, the external fluid-impermeable sheet encloses the absorbing pad across its entire thickness, then is folded back along the longitudinal edges of the inside (near the body) of the pad which thereby is wholly inserted into an open, impermeable pocket opposite its absorbing side.

Again in the same manner, the external impermeable sheet comprises sideways extensions on which in this case are fastened elastically extending elements to assure the hermeticity of the crotch.

Other advantages and features of the invention will become clear in the description below of two illustrative embodiments accompanied by a drawing.

Figure 4:
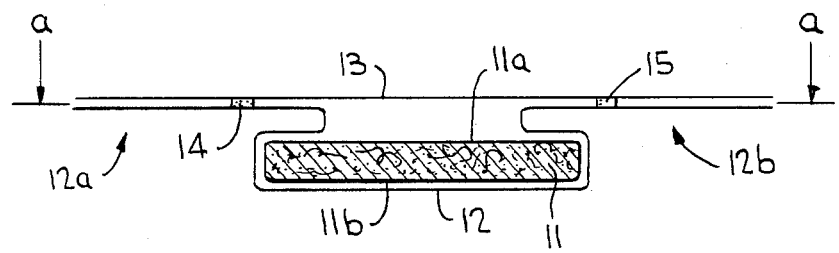
Figure 5:
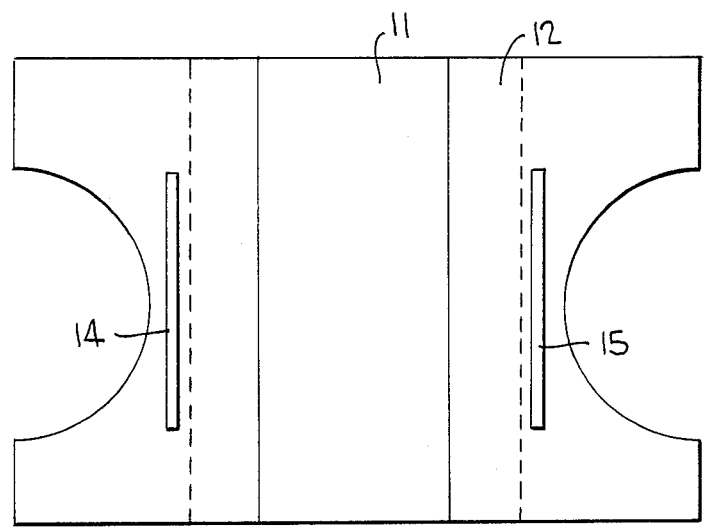

FIGS. 4 and 5, respectively, show in cross-section and top view a disposable pilch of the present invention.

Figure 1:
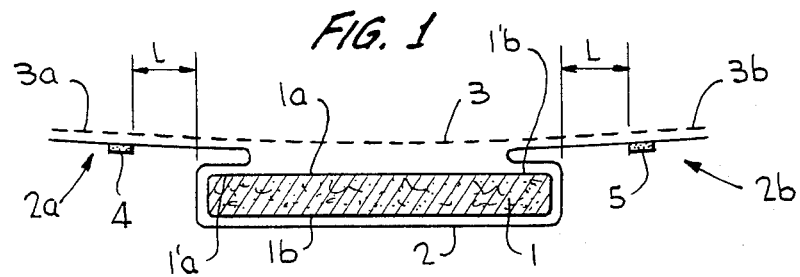
FIG. 1 is a cross-section of a menstrual napkin of the present invention.
Figure 2:
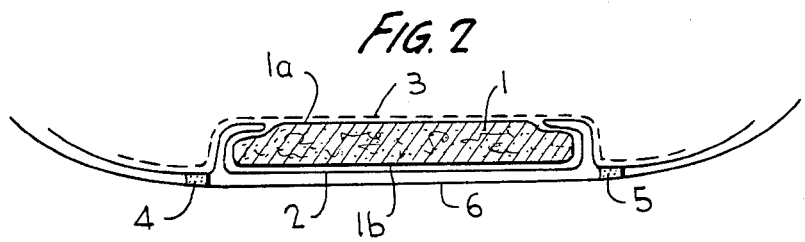
FIG. 2 shows the same menstrual napkin in cross-section when fastened to underwear.

The drawing of FIGS. 1 and 2 shows a menstrual napkin comprising an absorbing pad 1 with a side 1a directed toward the user's body and an opposite side 1b, where this absorbing pad 1, for instance, can be a cellulose fiber pad or a "fluff" pad.

The pad is enveloped by a liquid-impermeable sheet 2 preferably made of plastic (for instance polyethylene) which covers the pad side 1b and then all of its thickness and is also applied by being pleated on the longitudinal edges 1'a and 1'b of the pad side facing the user's body. The absorbing pad 1 consequently is inserted into a "pocket" of impermeable material except for the larger part of its side directed at the user's body, which constitutes the absorption surface.

In turn, the impermeable sheet 2 is folded on itself above the said pleats at the longitudinal edges to form sideways extensions 2a and 2b which extend beyond the surface bounded by the absorbing pad.

Adhesive strips 4 and 5 are deposited on the sideways extensions 2a and 2b, respectively, and are meant to fasten the napkin to underwear symbolized by the reference 6 in the drawing of FIG. 2.

A liquid-permeable sheet referenced by 3 clads the upper part of the sanitary article. This permeable sheet can be fastened to the impermeable sheet 2 by means of lines of adhesive 3a, 3b for instance. Such an arrangement of the impermeable sheet on the permeable one makes it possible to keep the pleats of the impermeable sheet 2 on the longitudinal edges 1'a and 1'b of the pad side 1a.

The adhesive strips 4 and 5, to keep the napkin in position, are located at a distance "1" from the respective edges of the absorbing pad which is fit to permit fastening to the underwear 6 as shown in the drawing of FIG. 2.

Preferably, the distance "1" is selected to be close to the thickness of the compressed pad.

The napkin is shown in the operational position in the drawing of FIG. 2. In view of the arrangement of the adhesive strips 4, 5 serving to keep the napkin in place, this napkin is kept under transverse tension, whereby the largest possible contact area is assured between the absorbing mass of the menstrual napkin and the body of the user.

Also, the arrangement of the adhesive strips offers the advantage of tensioning the liquid-permeable sheet which is in contact with the user's body for improved absorption and improved safety.

Figure 3:
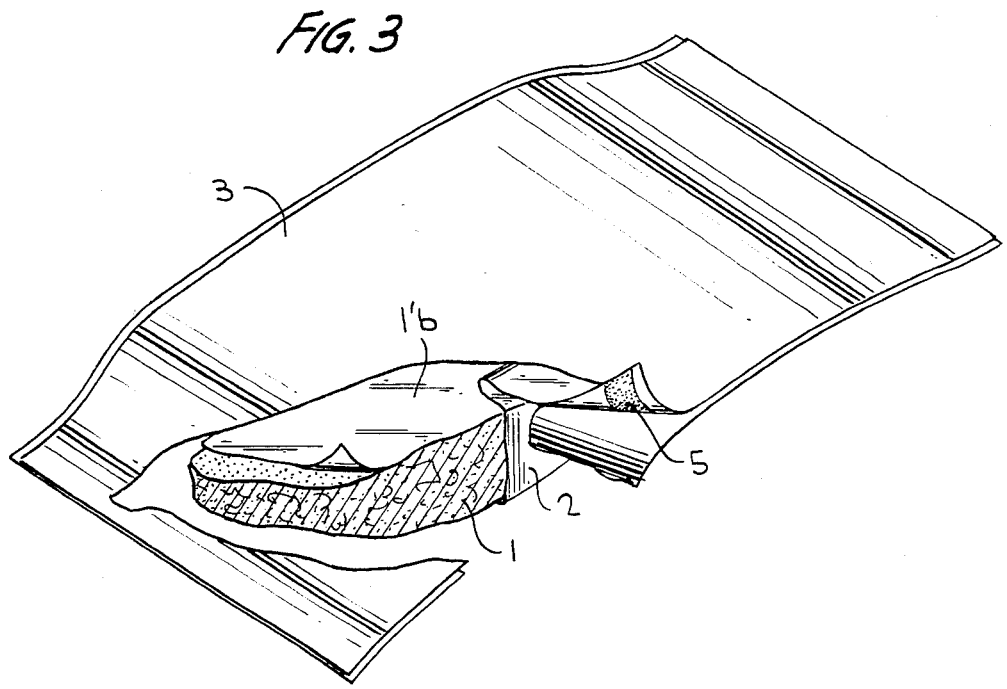
FIG. 3 is a perspective of a menstrual napkin of the same type with a multilayer absorbing pad.

The drawing of FIG. 3 shows the menstrual napkin of the invention with an absorbing pad consisting of two layers of "fluff," where the layer near the body is less compressed than the other. Again it is possible to introduce in manner known per se particles of a high fluid-absorbing product into the mass of the pad.

The lines of adhesive 4 and 5 advantageously are covered with a protective paper with, for instance, one silicone-treated side, in manner known per se.

The drawing of the FIGS. 4 and 5 shows a pilch of the invention. It consists of a stratified structure comprising an absorbing pad 11, an external liquid-impermeable sheet 12, and a liquid-permeable sheet 13.

As in the case of the above-described menstrual napkin, the impermeable external sheet is pleated along the longitudinal edges of the pad side 11a facing the user's body (infant or incontinent adult).

The sideways extensions 12a, 12b are provided with elastically extending elements 14, 15 which, for instance, can be natural or synthetic rubber straps positioned in the stressed state in the area of the crotch.

A fluid-permeable sheet referenced by 3 is fastened to the assembly consisting of the absorbing mass and the "pocket"-shaped external sheet.

Such a structure is characterized by a particular shape of the external fluid-impermeable sheet and offers the advantage of forming a barrier against lateral leaks while preserving the largest possible absorption surface in contact with the body.

I claim:

1. Sanitary article to absorb body liquids of the type including an absorbing-material pad (1, 11) with one side facing the human body, clad by a liquid-permeable sheet (3, 13) to be in contact with the body, and an opposite side, clad by an external liquid-impermeable sheet (2, 12), characterized in that said external liquid-impermeable sheet (2, 12) envelops said pad on said opposite side (1b, 11b) over the entire thickness of said pad and then is pleated along the longitudinal edges of that pad side (1a, 11a) which faces the human body so as to extend beyond each longitudinal edge to form sideways extensions (2a, 2b/12a, 12b) beyond the surface bounded by the absorbing pad (1, 11).

2. Sanitary article per claim 1, characterized in that said liquid-permeable sheet is fastened to the liquid-impermeable sheet at latter's lateral parts.

3. Sanitary article per one of claims 1 and 2, to absorb body liquids, characterized in that means (4, 5) fastening said article onto underwear are provided on each lateral part (2a, 2b) and at a distance from the absorbing pad substantially equal to the thickness of said pad when it is compressed.

4. Sanitary article per claim 3, characterized in that said fastening means (4, 5) are continuous or interrupted lines of adhesive.

5. Sanitary article per claim 4, characterized in that said lines of adhesive (4, 5) are covered by a protective strip, preferably a paper tape with a silicone-treated side.

6. Sanitary article per either of claims 1 and 2, to absorb body liquids, of the disposable pilch type, characterized in that an elastically extending element (14, 15) is provided at least in the crotch on each lateral part (12a, 12b).

7. Sanitary article of the disposable pilch type, per claim 6, characterized in that said elastically extending elements (14, 15) are rectilinear and located outside the surface bounded by the absorbing pad.

* * * * *